United States Patent [19]
Nicolau et al.

[11] Patent Number: 5,017,359
[45] Date of Patent: * May 21, 1991

[54] AEROSOL COMPOSITIONS FOR IN VIVO IMAGING AND THERAPY

[75] Inventors: Yves-Claude Nicolau, La Chapelle; Alain LePape, Langeais; Rita Barot-Ciorbaru, Fontenay-aux-Roses, all of France

[73] Assignee: Centre National de la Recherche Scientifique, France

[*] Notice: The portion of the term of this patent subsequent to Jul. 3, 2007 has been disclaimed.

[21] Appl. No.: 930,409

[22] Filed: Nov. 12, 1986

Related U.S. Application Data

[63] Continuation-in-part of Ser. No. 794,500, Nov. 1, 1985, abandoned.

[51] Int. Cl.$^5$ .............. A61K 43/00; A61K 49/00; A61K 49/02; A61K 9/127
[52] U.S. Cl. .................... 424/1.1; 424/7.1; 424/9; 424/450; 428/402.2; 436/829; 514/772; 514/773
[58] Field of Search ............... 424/1.1, 450, 7.1, 9, 424/85

[56] References Cited

U.S. PATENT DOCUMENTS

| | | | |
|---|---|---|---|
| 4,042,678 | 8/1977 | Ciobaru et al. | 424/12 |
| 4,201,768 | 5/1980 | Ciorbaru nee Sfartz et al. | 424/92 |
| 4,280,991 | 7/1981 | Burch | 424/1.1 |
| 4,396,607 | 8/1983 | Lefrancier et al. | 424/177 |
| 4,409,209 | 10/1983 | Baschang et al. | 424/177 |
| 4,544,545 | 10/1985 | Ryan et al. | 424/1.1 |
| 4,590,060 | 5/1986 | Ehrenfeld | 424/1.1 |

OTHER PUBLICATIONS

Dictionary of Microbiology, Wiley & Sons (Pub.), p. 1055, (1980).
McGraw-Hill Dictionary of Scientific and Technical Terms, 3rd ed., (1984), p. 257.

Primary Examiner—Richard D. Lovering
Assistant Examiner—John M. Covert
Attorney, Agent, or Firm—Handal & Morofsky

[57] ABSTRACT

The present invention relates to an aerosol composition for in vivo imaging or ex vivo diagnosis of tumors, which composition contains one or more soluble fragments of bacterial wall or cell peptidoglycan or equivalent synthetic compounds which are labelled with a radioactive, paramagnetic or fluorescent element and encapsulated in liposomes and a substrate which can be used for administration by aerosol.

10 Claims, 18 Drawing Sheets

FIG_1

Macrophage-tumor cell cultured:
○ : addition of NSPD (20μg/ml)
● : addition of monokines and NSPD
□ : control
▲ : addition of monokines (1:3, v/v)

Points represent the mean of 2 to 3 experiments with triplicate samples in each experiment ± SD

AEROSOL COMPOSITIONS FOR IN VIVO IMAGING AND THERAPY

CROSS REFERENCE TO RELATED APPLICATION

This application is a continuation-in-part of U.S. patent application Ser. No. 794,500 filed Nov. 1, 1985 now abandoned.

The present invention relates to compositions intended more especially for in vivo imaging, mainly by scintigraphy but also by other diagnostic techniques, such as nuclear magnetic resonance or fluorescence. The present invention is also applicable to the ex vivo diagnosis of tumors in using fluorescent or radioactive antibodies dressed against the composition active principle.

Further, since the active principle fixes itself in vivo on various tumors, it can be used as a targeted carrier in order to transport drugs towards these tumors.

At last, this active principle can be used for immunotherapy, mainly for tumor treatments.

In vivo imaging techniques by scintigraphy are known, and consist in using a vector agent labelled with a radioactive element, which vector agent becomes bound specifically to cells which it is desired to visualize. This type of examination is used, in particular, for detecting and demonstrating pathological conditions involving tumors and those involving inflammation.

The compositions according to the present invention were shown to be especially effective in this type of application.

The present invention deals with an aerosol composition for application to human or animal body, characterized in that it comprises one or more soluble fragments of bacterial wall or cell peptidoglycan encapsulated in liposomes and a substrate which can be used for administration by aerosol.

More especially, these compositions may be aerosol compositions for in vivo imaging or ex vivo diagnosis of tumors, which compositions contain one or more soluble fragments of bacterial wall or cell peptidoglycan or equivalent synthetic compounds which are labelled with a radioactive, paramagnetic or fluorescent element and encapsulated in liposomes and a substrate which can be used for administration as an aerosol.

These compositions may be compositions for therapy wherein the one or more soluble fragments of bacterial wall or cell peptidoglycan or equivalent synthetic compounds are used for immunotherapy or as a targeted carrier for a drug bound to them.

As it will be demonstrated, the compositions may be used for immunotherapy especially in the treatment of cancer but may be used also for targeting active drugs such as cytotoxic or cytostatic drugs to the tumor cells, such a targeting and the corresponding technologies are well known in the art.

In addition to that a particular fraction of Nocardiae named Nocardia Soluble Peptidoglycan derivative (NSPD) may be used for immunotherapy and as targeted carrier, especially in combination with Monokine in injectable form.

Soluble peptidoglycans and fractions containing soluble fragments of peptidoglycans originating from the bacterium or bacterial wall of Nocardiae have been described in French Patents 2,345,158, 2,268,531 and 2,345,159 (U.S. Pat. Nos. 4,042,678 and 4,201,768).

These are peptidoglycans extracted from the essentially delipidized and deproteinized walls or from the cells of three strains of Nocardia, N. opaca, N. corallina and N. rubra, which are delipidized, treated with enzymes and subjected to various purification processes.

The fractions obtained have a multiplicity of potentialities in addition to their mitogenic activity (R. Ciorbaru et al., Infect. Immun. 1975, 11, 257). These fractions possess a range of other properties, such as antitumor activity (R. Barot-Ciorbaru et al., Int. J. Immunopharmacol. 1981, 3, 115), capacity to induce circulating interferon (R. Barot-Ciorbaru et al., Infect. Immun. 1978, 19, 353 and J. Reticuloendothel. Soc. 1981, 30, 247), to activate NK cells (R. Barot-Ciorbaru et al., J. European, Jerusalem Congress Sept. 8–13, 1985), and to inhibit the growth of pulmonary metastases (R. Barot-Ciorbaru et al., Forum de Cancérologie, Paris 10–11-/VI, 1985). Macrophages are directly or indirectly involved in most of these activities; in effect, the addition of these fractions to mouse or rat resident peritoneal macrophages causes them to secrete, in addition $IL_1$ and other monokines (R. Barot-Ciorbaru et al., C.R. Acad. Sc. Paris 1984 v. 298, series III, No. 17).

Furthermore, it is possible to substitute these fragments by equivalent synthetic compounds, that is compounds obtained by synthesis or hemisynthesis, and including in their formula elements of structure contained in the said soluble fragments mentioned before. It could be especially a simplified synthetic structure the manipulation of which is easier.

N. opaca ATCC 21,953, synonymes Mycobacterium opacum or Proactinomyces opacus, cells (gram-positive, aerobic, nonpathogenic) are cultured in accordance with the conditions described in the abovementioned patent. The culture time of 48 hr. can be reduced to 24 hr.

The bacterial cells obtained are separated from their culture medium by centrifugation. The moist cells are subsequently subjected to a treatment for extraction of the lipids which they contain, using one or more organic solvents.

The cells are initially suspended in 30 times their weight of acetone at room temperature for 48 hours on a magnetic stirrer. This procedure is repeated several times. The cells are then delipidized under reflux in a Soxhlet type extractor using pure solvents (acetone, alcohol, ether, chloroform or an 83:17 chloroform/methanol azeotropic mixture). The total extracted lipids reach 40% of the dry weight of the cells. The cells are then resuspended in acetone, decanted and dried.

The delipidized cells are suspended in 100 times their weight of water, and 0.2 mg of DNase per 100 ml of suspension is added to destroy the deoxyribonucleic acid. The suspension is centrifuged at 27,500 g and at 40° C. for one hour.

The cells are again suspended in 0.1M ammonium acetate at pH 6.2 in the presence of 0.1% of chicken egg white lysozyme, and then incubated for 10 hours at 37° C., a few drops of toluene being added to prevent contamination.

The suspension is centrifuged and the cells are incubated a second time under the same conditions. The two extracts are mixed, lyophilized and taken up with water to remove the ammonium acetate.

The two extracts obtained are then delipidized by three successive extractions at room temperature with ether, and then dried. 500 mg of Nocardia extract are placed on a Sephadex G-75 column equilibrated with 0.1M acetic acid, and eluted with the same solution. The fraction known as NSPD (NSPD: nocardia soluble peptidoglycan derivative) consists of 18-20 4-ml tubes, the content of which is opalescent, and the tube contents are reunited and lyophilized. The NSPD fraction represents 50% of the pool of the starting material.

NSPD is a white powder which has a flocculent appearence. It is soluble in water alkalinized with 0.1M NaOH pH 10.5 or in 0.03M sodium citrate, 0.5M NaCl at pH 9.4.

The elementary chemical analysis shows the following values:

| CONTENTS EXPRESSED AS GRAMS PER 100 g OF PRODUCTS | | | | |
|---|---|---|---|---|
| C | H | N | S | P |
| NSPD 14.57 | 5.82 | 11.64 | 0.16 | 3.05 |

| NSPD is heterogeneous. It contains: | |
|---|---|
| neutral sugars | 25-30%. |
| amino sugars | 19-25%, |
| amino acids | 32-35%, |
| DAP (diaminopimelic acid) | 200 nmol/mg, |
| Lipids | 7%. |

Its heterogeneity could be further demonstrated by means of several techniques:
by electrophoresis in denaturing medium, 43000 to 5000 apparent molecular mass subfractions can be demonstrated;
by sedimentation at a speed of 59;780 rpm at 20° C. in phosphate buffer $\mu=0.1$, pH 11.8 at a concentration of 5 mg/ml/ A peak is obtained which is not clearly separated and represents a heterogeneous mixture of the products (Beckman ultracentrifuge);
by treatment with Folch's mixture (chloroform/methanol/water, 16:8:6 v/v), after 16 hours 3 phases are obtained; 50% aqueous, 30% organic and 20% interphase;
by molecular sieve HPLC chromatography on a TSK 2000 column, 4 fractions are obtained.

The NSPD according to the present invention is hence characterized by its heterogeneity since, depending on whether it is treated with Folch's mixture or whether it is subjected to HPLC, 3 phases or 4 distinct fractions, respectively, are obtained.

Furthermore, after separation by HPLC, the NSPD activity can be found in one or more fractions.

It is of course possible, as described in the patents already mentioned, to use peptidoglycans originating from walls of other bacteria, but in the context of the present invention it will be preferable to use in particular the abovementioned derivative referred to as "NSPD" which originates from a strain of Nocardia.

The NSPD is labelled with a compound and, for reasons of convenience, this compound will, for the most part, be radioactive. $^{99m}$Tc (technetium), the technique for labelling of which is reliable and rapid, and the half-life of which enables scintigraphic examinations to be carried out on man, will preferably be used.

As regards the liposomes employed, these can be multilamellar liposomes (MLV) or unilamellar liposomes (ULV), more especially consisting of phospholipids, such as dipalmitoyl phosphatidylcholine and phosphatidylserine, and cholesterol, especially in the mole ratio 4:1:5.

These liposomes can be produced according to known techniques, for example by the process of Bangham by hydration of lipids (J. Mol. Biol. 1965, 13, 238-252), by reverse phase evaporation (REV) according to Szoka and Papahadjopoulos (Proc. Nat. Acad. Sci. U.S.A., 1978, 75, 4194-4198) or by sonication of a dispersion of phospholipids (Biochemistry, 1977, 16, 2806-2810), and the like.

The trials performed showed that identical results were obtained from liposomes the size of which was between 50 nm and 500 nm and which had to consist of at least one phospholipid compound possessing surfactant properties.

Encapsulation of the NSPD can be performed by adding it to the aqueous phase during the formation of the liposomes, or possibly by incubation with the liposomes for 30 minutes at 20° C. with intermittent stirring, taking into account the amphiphilic nature of NSPD.

The essential characteristic of the compositions according to the present invention is that they are used for administration by aerosol.

The trials performed showed, in effect, that no administration route other than by aerosol led to any satisfactory result.

Naturally, the formation of the aerosol from the composition of liposomes and NSPD may be produced by known techniques, employing suitable systems which will have to deliver particles of diameter less than 10 micrometers, most commonly using air as a carrier gas.

It is, however, recommended, when carrying out and implementing the inhalation process, to take care to avoid external contamination of the patients by the radio-active product in aerosol form, in order to avoid falsely positive scintigraphic results. It is also recommended to install a suitable aspiration device designed to prevent contamination of the air in the premises by the radio-active product in aerosol form during administration to the patients.

The compositions according to the present invention can be made more specific by fractionating the NSPD extracts or by making use of other wall peptidoglycans.

The compositions according to the present invention agree with peptidoglycans bound NSPD or peptidoglycan fragments. However, delipidation and acetic acid treatment followed by centrifugation allow the preparation of a precipitated fraction free of peptidoglycan. Same scintigraphic results can be obtained even if the material is administered under the same conditions as NSPD. For each of these fractions, it will naturally be appropriate to determine their specificity.

The hypothesis that NSPD is bound to tumors infiltrating activated macrophages has been laid down from tumors imaging results and others biological data. In order to control this one, p388D1 macrophages in DB/A2 mice have been activated by E. coli 260 lipopolysaccharide (LPS). A day after LPS administration, peritoneal macrophages were collected and their activation controled by the chemoluminescence assay. 24 hours after LPS macrophage activation, $^{99m}$ Technetium labelled and in liposome encapsulated NSPD was administered by aerosol to mice. After 2 hours, the radioactive NSPD fixation rate was calculated on macrophages.

The same experiment was carried out on control mice not having received macrophages activators. (For experiments on activated P388D1 macrophages animals received I.P. 50 μg of unlabeled NSPD or LPS 1 day before the test.)

The results shown in FIG. 9, demonstrate significant NSPD fixation to activated macrophages and its insignificant rate on control macrophages. In the third animals lot, the previously performed activation with unlabelled NSPD in substitution of LPS leads to the same results.

Identical results were obtained in using immunofluorescent techniques with antibodies prepared in rabbit against NSPD. After examination by fluorescent microscopy or by a cell screeing system, it can be confirmed that NSPD fixation occurs especially on preactivated macrophages population.

Other advantages and characteristics of the invention will emerge on reading the examples and figures which follow.

BRIEF DESCRIPTION OF THE DRAWINGS

FIGS. 8 and 8A-8B show the percentage of lysis of [$^{14}$C]inosine-labeled 3LL tumor cells induced by identical populations of thioglycollate-elicited peritoneal macrophages either previously primed with macrophages activating factor (A) or simply preincubated with culture medium (B) as control.

EXAMPLE 1

Pharmacological Data

The scintigraphic examinations described below were carried out with NSPD preparations which were shown to be active for the detection of pulmonary carcinomas and metastases after obtaining the consent of the patients and the agreement of the Commission d'Ethique [Ethical Commission] of the Centre Hospitalier Universitaire of Tours (France).

After monitoring the sterility and absence of pyrogens (in vivo test in rabbits and "Limulus test", Mallinckrodt, Inc., in vivo), the preparations dissolved in isotonic saline solution are labelled with the $^{99m}$Tc-Sn complex according to the following procedure derived from the technique of Osborne et al. (Int. J. Nucl. Med. Biol., 1982, 9, 47–51): 400 µg of Lyophilized NSPD dissolved in 400 µl of 0.15M NaCl are reduced under vacuum with 60 µg of anhydrous stannous chloride for 15 minutes, and then complexed with 40 to 80 mCi of 99m-(sodium pertechnetate) eluted at the time of use with 0.15M NaCl solution from a generator (C.E.A., France).

The labelling yield of the NSPD preparation assessed by partition chromatography in methanol/water (70:30 v/v) solvent should be 99.5% at least.

This labelled preparation is then encapsulated in liposomes of dipalmitoyl phosphatidylcholine, phosphatidylserine and cholesterol, for example in the mole ratio 4:1:5.

The technique employed for preparing the liposomes is as follows: the phospholipids and cholesterol are mixed in chloroform. After evaporation of the solvent, the lipids are deposited as a film on the wall of the vessel, and the residual solvent is removed in 30 to 45 minutes under a stream of nitrogen. To the lipid film, PBS buffer at pH 7.4 is added, so as to obtain a final phospholipid concentration of 1 mg/ml in the aqueous phase. After sonication for 25 minutes at +2° C. under nitrogen, monitoring of the size of the liposomes is performed by electron microscopy.

After incubation under vacuum of 5 ml of liposomes and the labelled NSPD solution for 30 minutes at room temperature, the final preparation is sterile, pyrogen-free, of pH between 7.2 and 7.5 and contains less than 1% of free $^{99m}$Tc.

Figure 10:
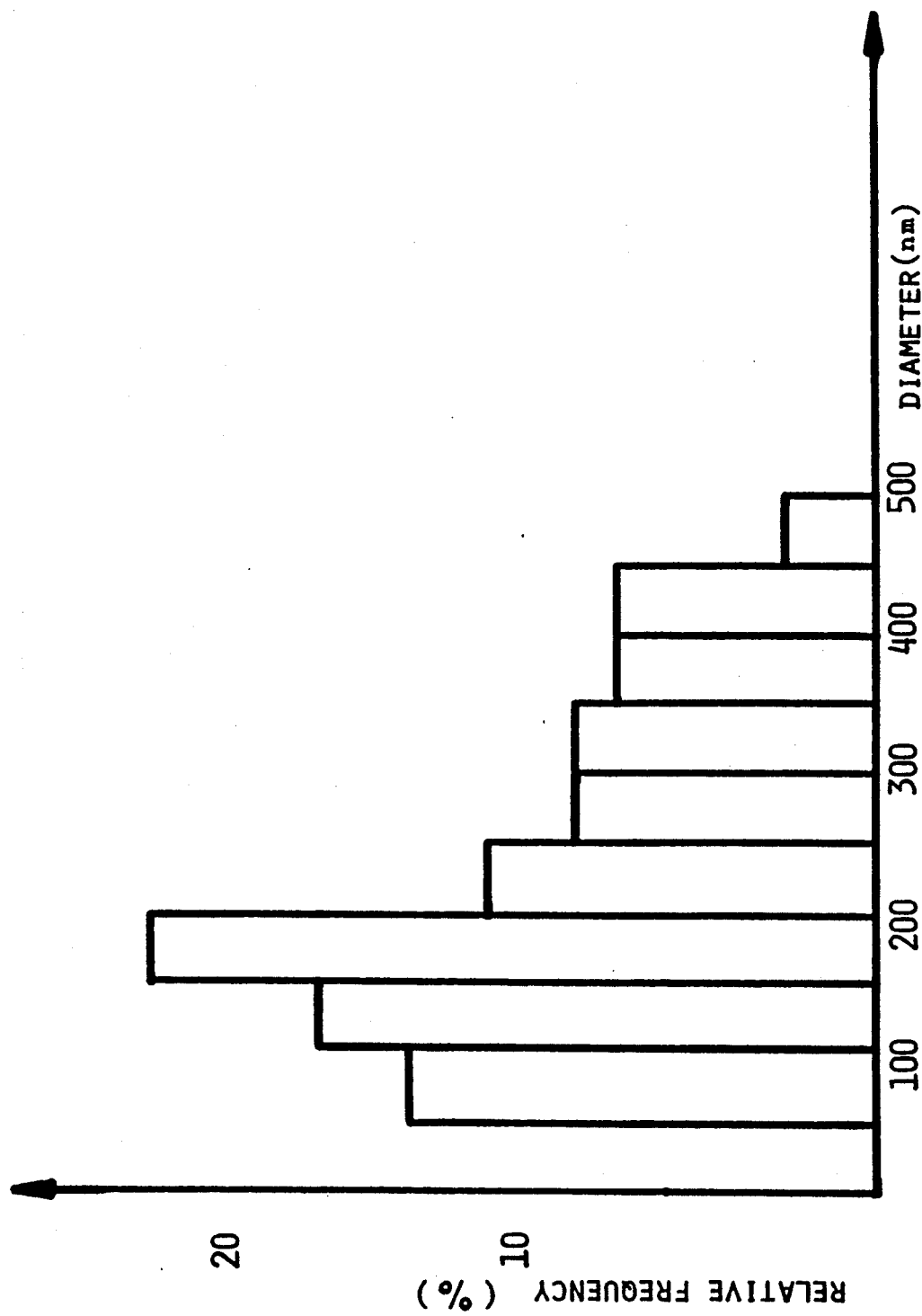
FIG. 10 shows the size distribution of liposomes in the preparation of Example 1.

This is the preparation which is administered to the patients using a TV 6000 Siemens ultrasonic microinhaler (Germany) in an E.S.I. air filtration hood (France). Size distribution of the liposomes in the preparation are shown in FIG. 10.

The pulmonary absorption pharmacokinetic examination in liposomes encapsuled or not and administered by aerosol $^{99m}$Tc-NSPD, was carried out on tracheotomized dogs.

The results show that there is almost no NSPD passage in blood when it is administered alone and the passage is optimal after encapsulation in PC-PS-chol. liposomes. NSPD then quickly diffuses in lymph and free-cell liquids and is removed in urine with a 120±30 minutes biological half-life.

Other comparative assays were carried out with:

liposomes alone
NSPD in oleic acid
NSPD-PS liposomes
NSPD-PC liposomes.

Figure 1:
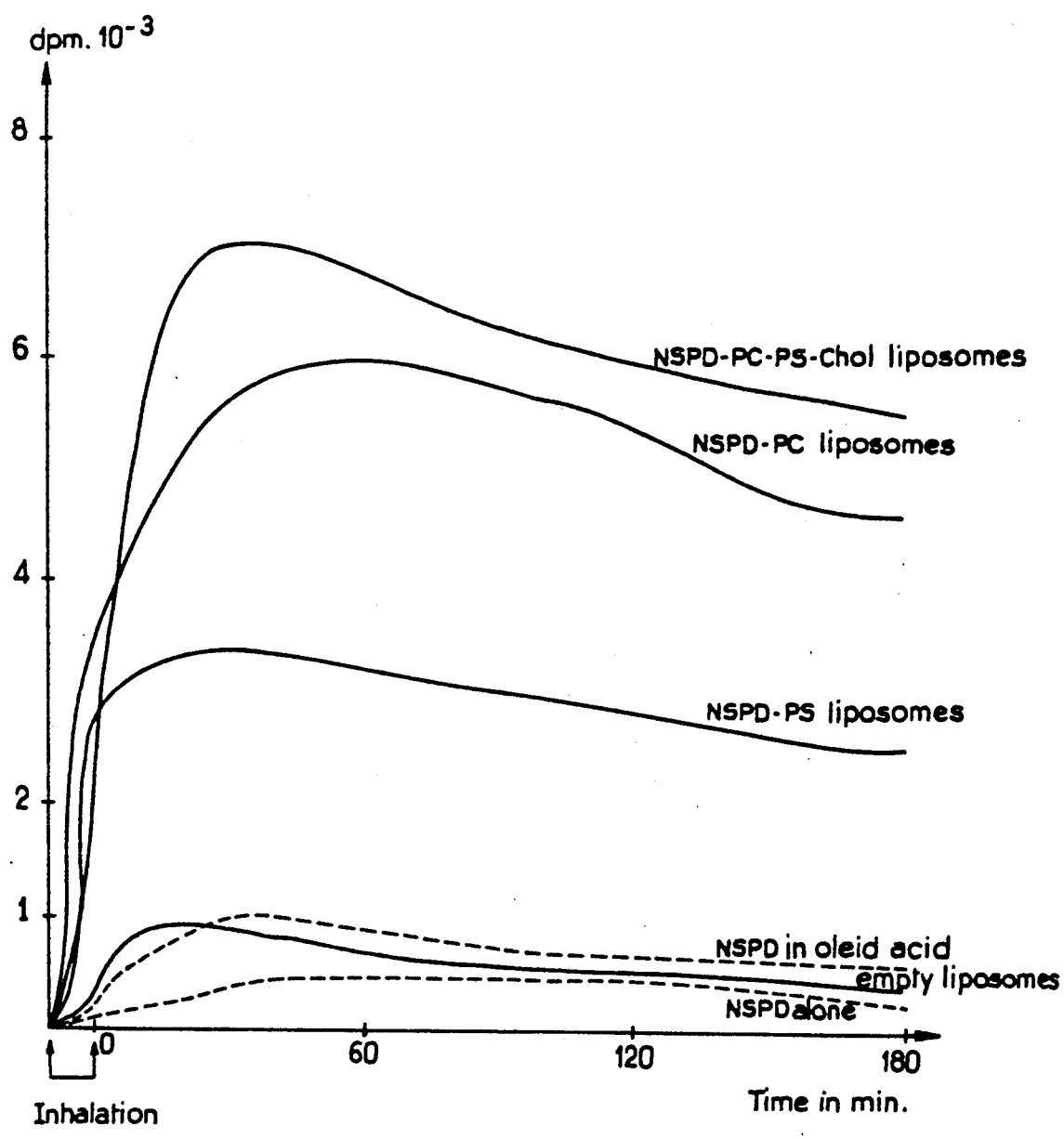
FIG. 1 shows the component radioactivities in blood after inhalation of various labeled preparations, as a function of time.

The results are shown in FIG. 1 which compares the component radioactivity in blood after inhalation of various labelled preparations, as a function of time.

EXAMPLE 2

Scintigraphic Data

The scintigraphic examinations are carried out from 1 hr. to 24 hr. after inhalation of the aerosol, with a Nuclear Chicago gamma camera equipped with a high resolution 140 keV parallel collimator, the data being processed on a SIMIS III computer (SOPHA MEDICAL-FRANCE).

The thyroid of the patients is protected from the binding of technetium possibly dissociated in vivo by administration of 400 mg of $NaClO_4$ per os 30 minutes before the beginning of the test.

To reduce the secretion of saliva and avoid premature contamination of the esophagus and digestive system, the patients also receive 0.25 to 0.50 mg of atrophine sulfate subcutaneously 45 minutes before the inhalation.

The examinations were performed initially on patients who had not received chemotherapy or radiotherapy for 1 month in order to avoid falsely negative results, but the final trials carried out led to generally satisfactory results with patients subjected to these therapies.

Patient 1

Figure 2:
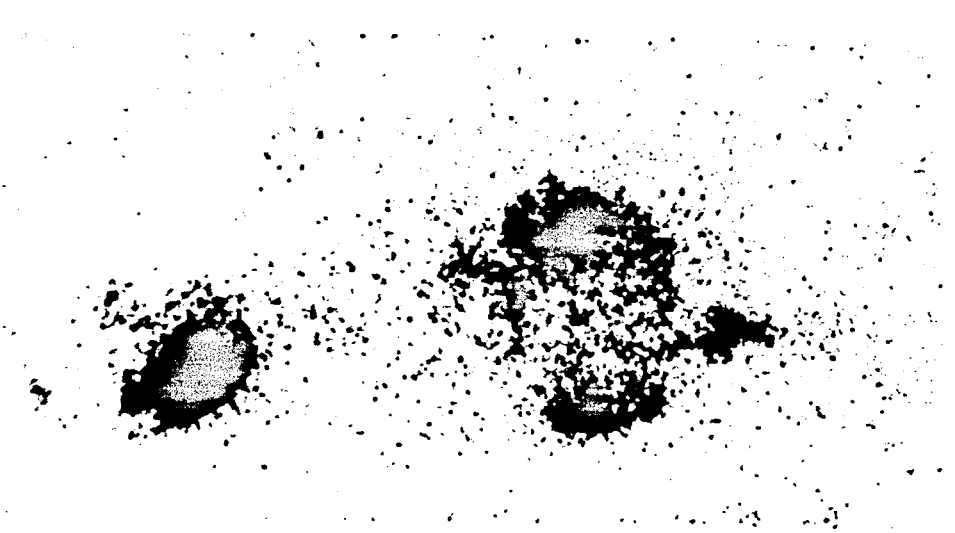
FIG. 2 shows the scintigrams of a patient no. 1 bearing a malignant melanoma of the right orbit and a metastasis on the dome of the skull.

The results of the imaging of patient 1 are shown in FIG. 2.

This figure shows the whole body scintigram of a patient bearing a malignant melanoma of the right orbit and a metastasis on the dome of the skull.

Image was produced after inhalation of $^{99m}Tc$-NSPD encapsulated in liposomes according to the procedure described in Example 1 (anterior face). The demonstration of the two tumors mentioned is noted and the background is very weak.

Patient 2

This patient has a non-keratinizing epithelial carcinoma of the right lung.

Figure 3A:
FIGS. 3A-3C show the results of scintigraphy after inhalation of liposomes containing 30 mCi of $^{99m}$Tc-NSPD (A and B) and monitoring of the ventilation with wenon 133 (C) in a patient no. 2 bearing a non-keratinizing epithelial carcinoma of the right lung (thorax posterior face).

FIG. 3 shows in A the different exposures of a dynamic scintigram (60 sec/image) obtained from 0 to 16 minutes during inhalation of the liposomes according to the present invention.

Figure 3B:
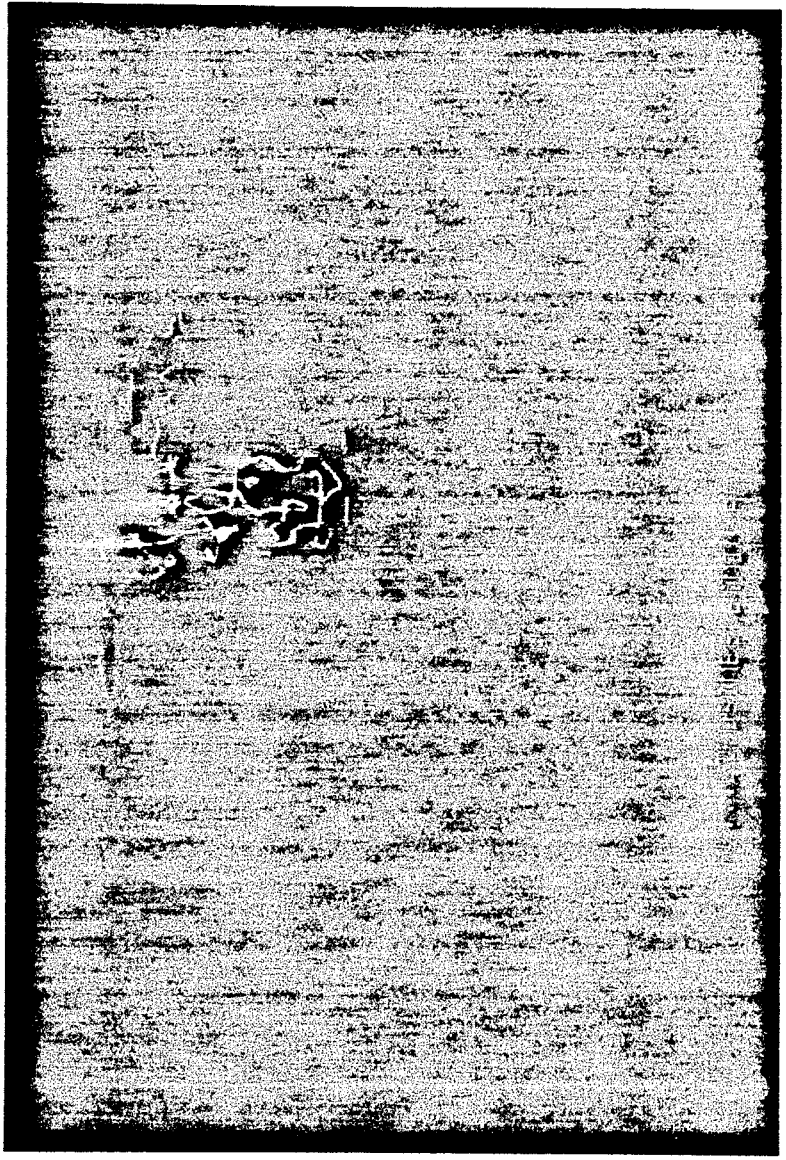

FIG. 3B, obtained 20 minutes after the beginning of the inhalation (static scintigraphy) shows objectively the hyper-binding of the tracer at the level of the right lung where the tumor is sited and the quantification of the radioactivity at the level of the region of interest and of the contralateral healthy zone.

Figure 3C:

FIG. 3C corresponds to the monitoring of the ventilation by xenon-133 scintigraphy. This examination shows objectively a hypoventilation of the tumor-bearing right lung in which 40% of the radioactivity is sited whereas the healthy left lung has an activity of 60%. This examination shows that the focus of early binding obtained with the $^{99m}Tc$-Sn-NSPD-liposome preparation and shown in FIGS. A and B genuinely results from an accumulation of the tracer in the tumor-bearing lung and does not correspond to an effect due to ventilation.

Patient 3

Figure 4A:
FIGS. 4A-4C show the scintigrams obtained 1 hour after inhalation of liposomes containing 30 mCi of $^{99m}$Tc-NSPD in a patient no. 3 suffering from infiltration of the thigh, the leg and the foot after ablation of a melanosarcoma of the sole of the right foot and a metastatic ganglion of the right groin. The views A, B and C correspond, respectively, to the thighs, knees and legs.
Figure 4B:
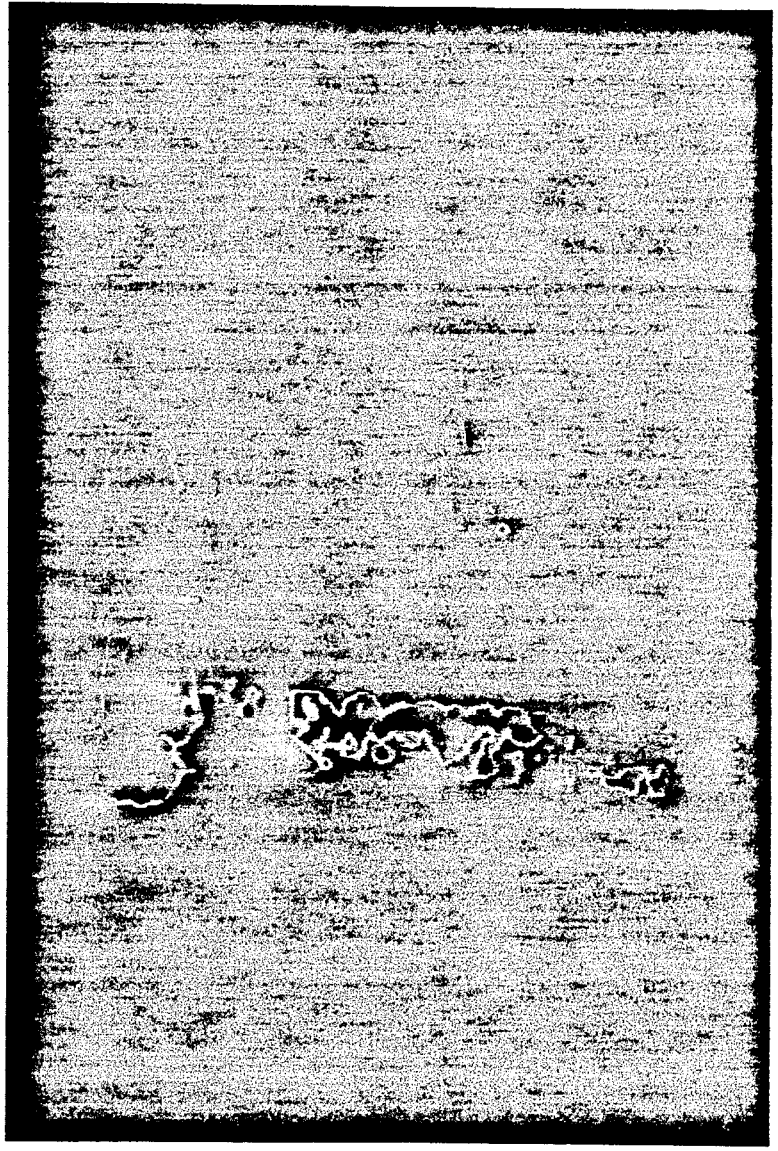
Figure 4C:
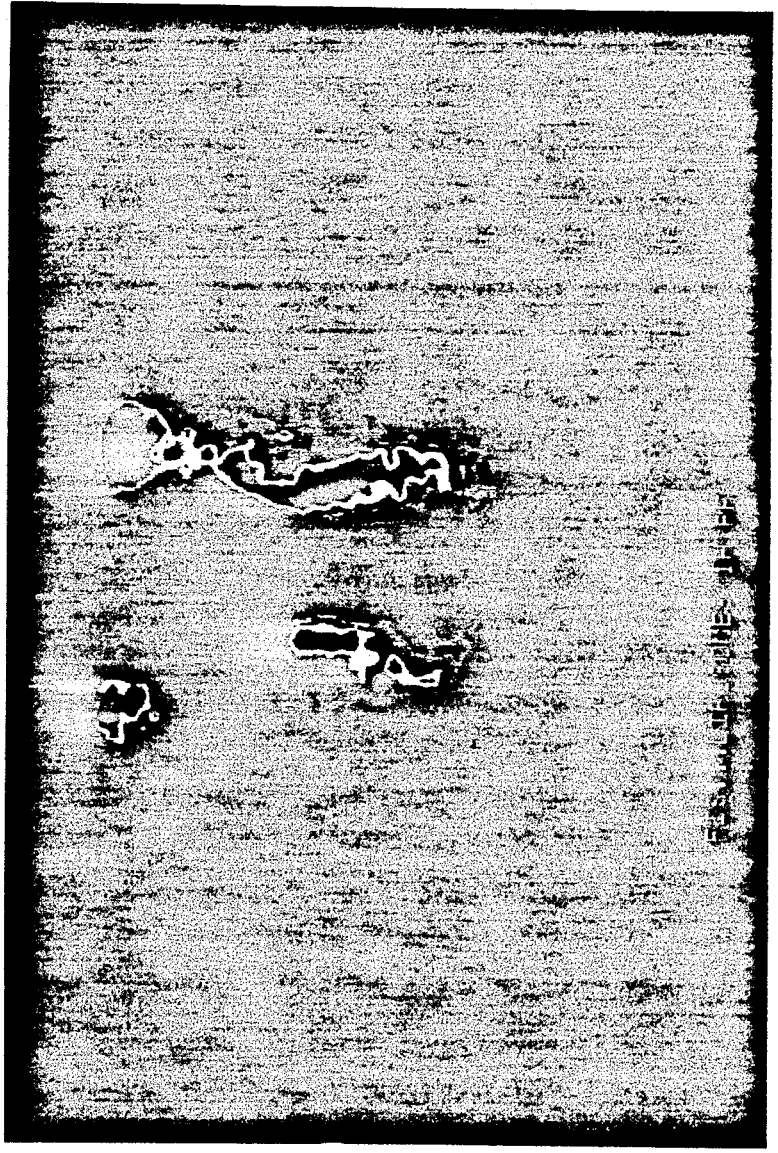

The scintigrams shown in FIG. 4 demonstrate the tumor infiltration of the right thigh (A) and the right leg (B) in the anterior face and the right foot (C) in the posterior face in a patient who underwent ablation of a melanosarcoma of the sole of the right foot and of a metastatic ganglion of the right groin. Scintigraphy is performed 1 hour after inhalation of liposomes according to the invention. Visualization of the tumor infiltration sited between the two excised tumors is very distinct by comparison with the same zones of the healthy contralateral leg.

Patient 4

Figure 5:
FIG. 5 shows the anterior face scintigram obtained 1 h 30 min after inhalation of liposomes containing 30 mCi of $^{99m}$Tc-NSPD in a patient no. 4 suffering from a metastatic ganglion of the right groin and a chain of subcutaneous metastases of a melanosarcoma.

FIG. 5 corresponds to the visualization of a chain of subcutaneous metastases of a melanosarcoma of the right thigh 1 h 30 min after inhalation of the liposomes containing labelled NSPD.

The tracer activity quantification in tumor area was performed by scintigraphic data processing and direct counting of the surgically excised tumor, few hours after inhalation. In both cases, the concentration factor in respect to reference healthy tissue were identical and respectively $1.35 \pm 0.5$ and $1.40 \pm 0.1$.

Patient 5

Figure 6A:
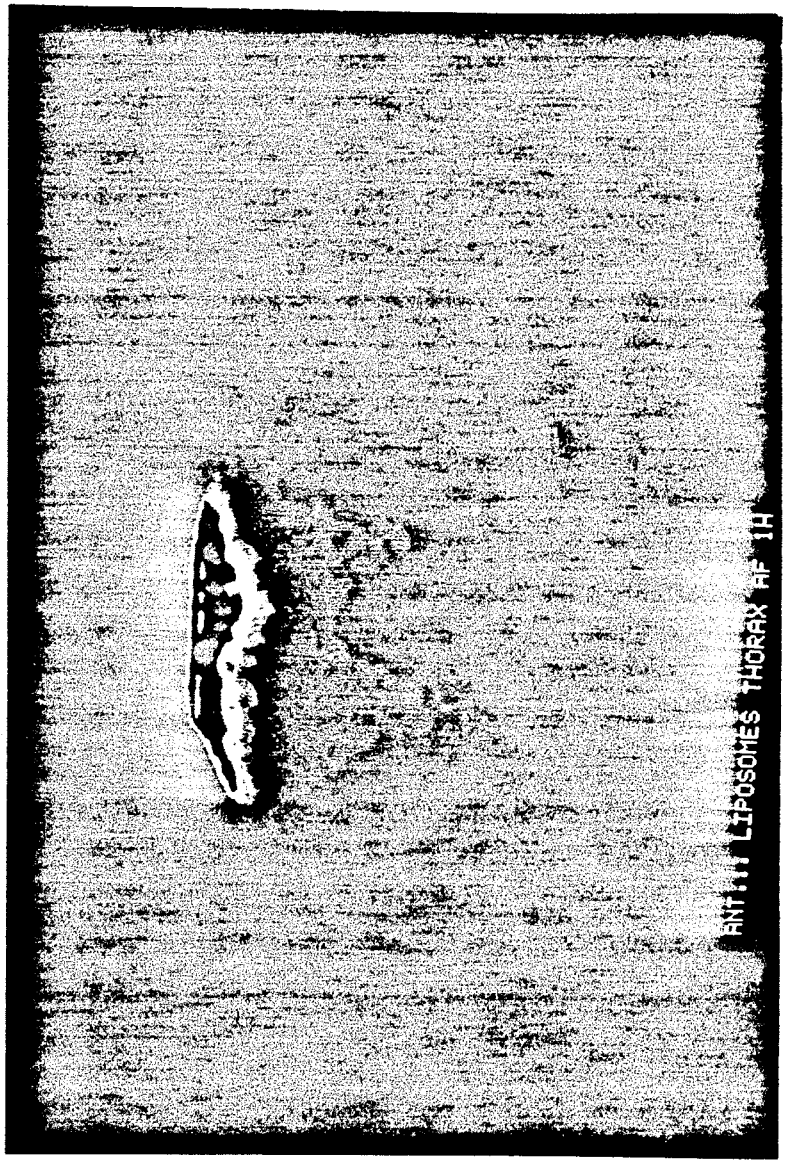
FIGS. 6A-6B show the scintigrams obtained 1 h (A) and 6 h (B) after inhalation of $^{99m}$Tc-NSPD encapsulated in liposomes by a patient no. 5 suffering from pulmonary metastases of a small cell carcinoma of the base of the tongue (thorax anterior face).
Figure 6B:
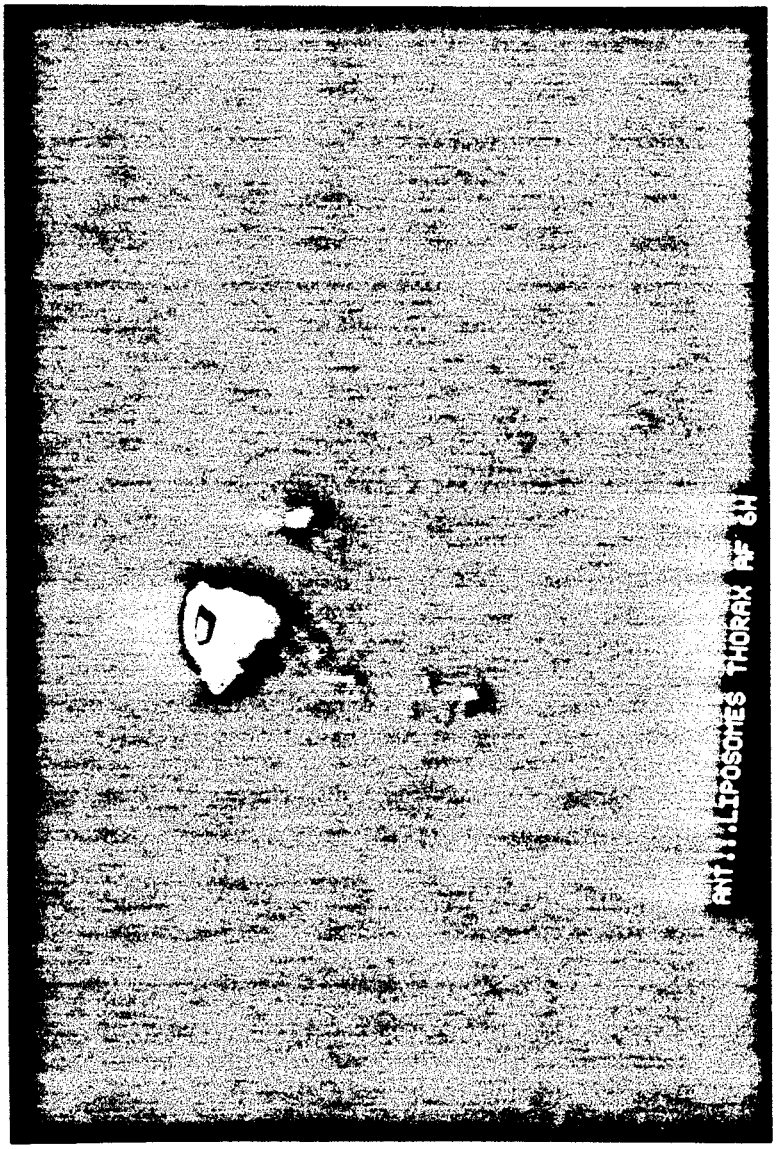

Visualization of pulmonary metastases of a small cell carcinoma of the base of the tongue (FIG. 6). Scintigrams obtained 1 h (in A) and 6 h (in B) after inhalation of 50 mCi of technetium according to the invention. There is an excellent correlation between the localization of the metastases obtained by scintigraphy at the sixth hour (in B) and the pulmonary radiological image.

Summary of scintigraphic results obtained on 51 patients which were carriers of primary or metastasic tumors confirmed by anatomopathological analysis, cervical and abdominal areas are contaminated during inhalation and are not taken into consideration.

| Number of patients | Type of tumor | Relative tumor concentration of the radiolabel | % of detected foci |
|---|---|---|---|
| 20 | metastatic melanoma | 1.20–2.10 | >85 inconstant fixation in bone |
| 8 | melanoma:residual disease | 1.20–1.50 | >80 |
| 10 | epidermoid bronchial carcinoma | 1.40–1.80 | >90 |
| 1 | poorly differentiated lung metastasis | 1.10–1.20 | >80 |
| 4 | other lung tumors | 1.10–1.60 | ≈70 |
| 1 | non malignant post trauma breast cytosteatonecrosis | 1.07 | — |
| 4 | non excised breast carcinoma | 1.30–2.00 | ≈50 |
| 3 | breast carcinoma: residual disease | 1.10–1.20 | ≈75 |

No significant fixation of NSPD is usually found in non-tumor inflammatory processes such as inflammatory granulomas and recent scars.

False positive fixation occured only in some joint inflammations and in mediastinal lymph nodes in sarcoidosis. False negative fixation has been observed in some bone metastases from malignant melanoma ($\approx 20\%$), tumor known to be very little infiltrated by macrophages.

Up to now, the smallest tumors detected by this method had a diameter of 4 millimeters, much less than the size required for X Computer tomography. Such a resolution may be attained in some cases by immunoscintigraphy. Nevertheless, due to possible antigenic variation in one and the same patients, immunoscintigraphy may not detect all metastases of a primary melanoma. Our method is not subject to such limitations.

A decisive advance which this invention makes is the detection of imperceptible residual disease in patients whose tumors have been surgically removed.

Figure 7:
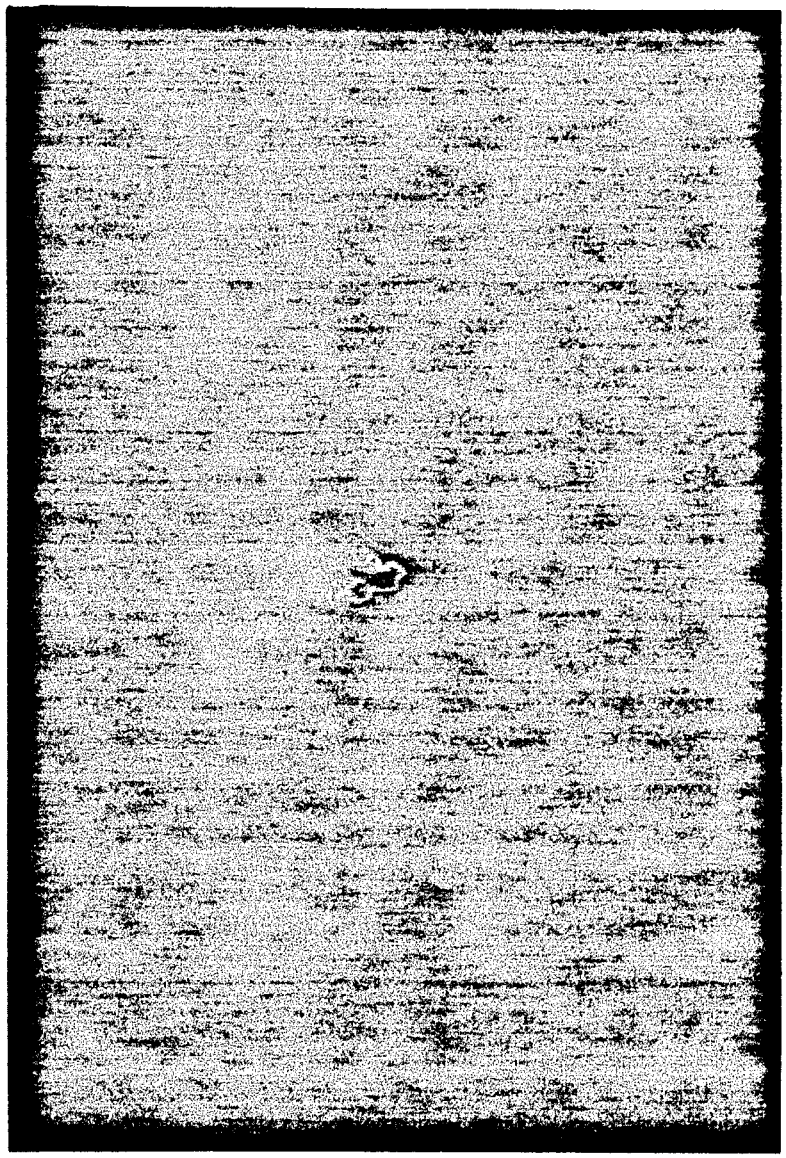
FIG. 7 shows the scintigraphy obtained after aerosol administration of $^{99m}$Tc-NSPD in liposomes to a patient operated several years ago and who was improperly pronounced free of tumor according to conventional tests.

As an example, FIG. 7 shows the scintigraphy obtained after aerosol administration of $^{99m}$Tc-NSPD in liposomes to a patient operated several years ago and, who, by all usual imaging investigations was pronounced free of tumor or netastases.

The scintigraphy of the thighs in anterior face shows, 1 h 30 min after inhalation, a tumor-infiltration of the Scarpa area which was confirmed histologically.

EXAMPLE 3

Anti-tumor Activity

It is well known that macrophages can obtain the ability to resist to tumor cells development under the influence of various stimulants. The isolated then injected to animals Nocardia fractions involve an increase of cytotoxic and cytolitic activity towards tumor-bearing targets as P815 mastocytoma and the C57B1/6 mouse 3LL Lewis carcinoma.

Figure 11:
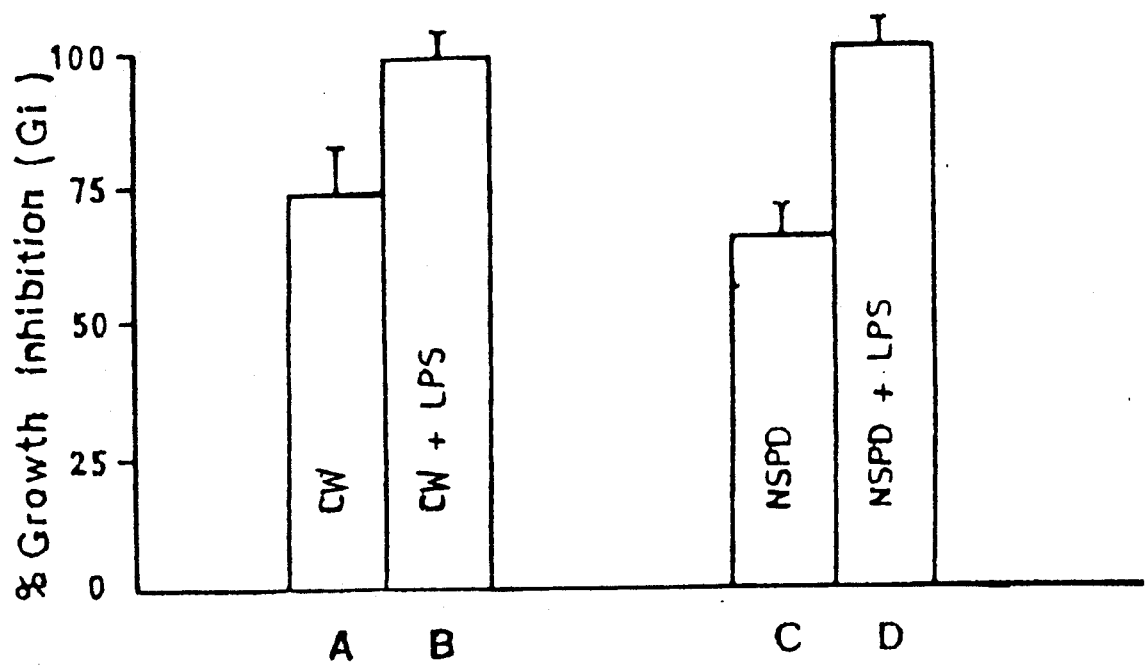
FIG. 11 shows the percent of growth inhibition of P185 cells in Example 3.

Percent of growth inhibition (GI) of P815 cells by:
A) CW-elicited macrophages
B) CW-elicited macrophages and LPS in vitro
C) NSPD-elicited macrophages
D) NSPD-elicited macrophages and LPS in vitro is shown in FIG. 11.

The % GI represents the efficiency of the treatment in inducing cytostatic activity according to the formula:

$$GI = 100 \times \frac{\text{cpm with control macrophages} - \text{cpm with treated macrophages}}{\text{cpm with control macrophages}}$$

Results are presented as the means of 6 independent experiments; ±SD.

This cytotoxic activity is able to involve in vivo regression of pulmonary micrometastases in Lewis carcinoma and the effect of these fractions is potentialised by combined administration of Monokines.

| Treatment of rats | Number of rats with invasion of local lymph nodes | Individual count of lung tumoral nodules | Median |
|---|---|---|---|
| water emulsion | | 0, 1, 4, 18, 69 | |

Effect of NSPD on the dissemination of the F6 transplanted rhabdomyosarcoma in the Wister AG rat.

Figure 8:
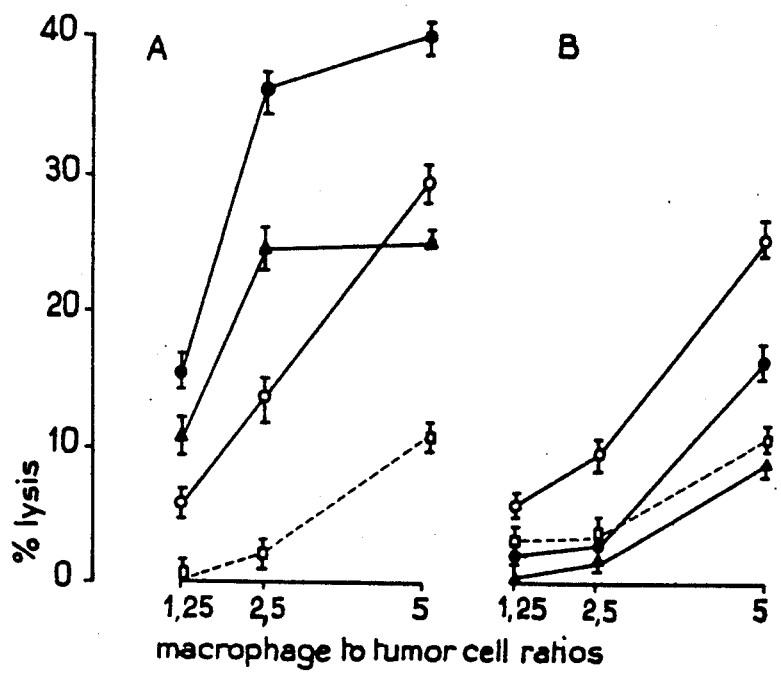
Figure 8A:
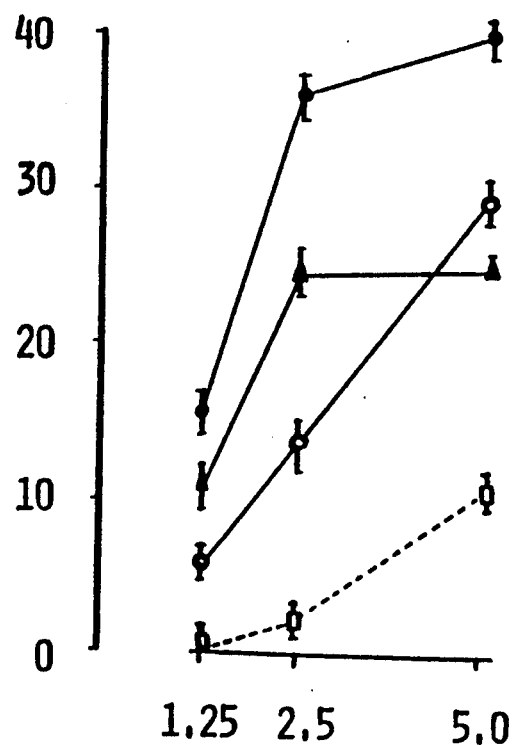
Figure 8:
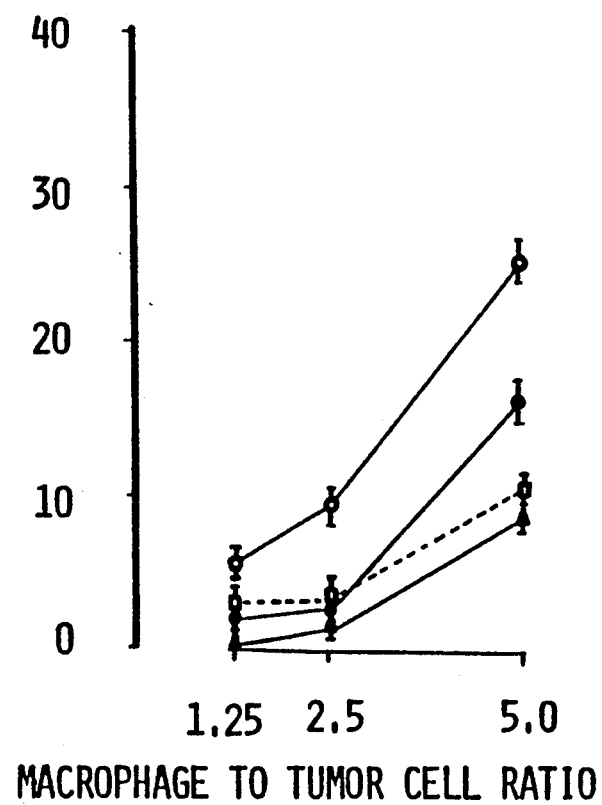
Figure 9:
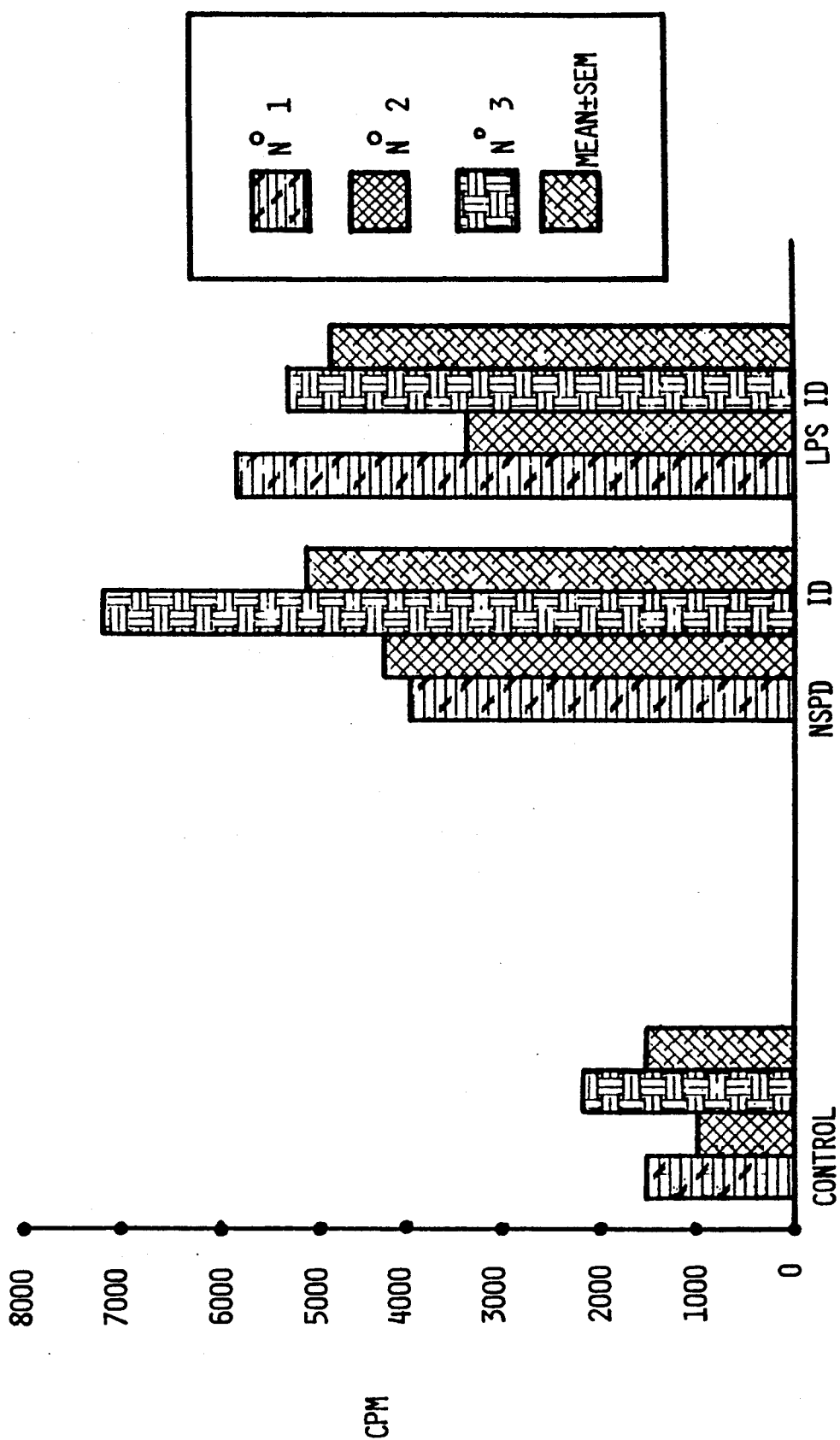
FIG. 9 shows the in vivo uptake of liposome encapsulated NSPD labelled with $^{99m}$Tc administered by aerosol to mice.

FIG. 8 shows the percentage of lysis of [$^{14}$C] inosine-labeled 3LL tumor cells induced by identical population of thioglycollate-elicited peritoneal macrophages either previously primed with macrophages activating factor (A) or simply preincubated with culture medium (B) as control.

It can also be noted in cells the presence of activation markers such as lysosomal enzymes and ectoenzymes like beta-galactosidase and alcalin phospho-diesterase.

| Type of Enzyme | Control Macrophages | NSPD stimulated macrophages |
|---|---|---|
| Lysosomal Enzymes | | |
| β-Galactosidase | 26 (±3) c | 9.5 (±0.1) |
| β-Glucuronidase | 9.9 | 21.2 (±0.2) |
| N-Acetyl-glucosaminidase | 76.7 | 195 (±2) |
| Acid phosphatase | 13.4 | 35.3 (±2) |
| Ekto-enzymes | | |
| Alkaline phosphodiesterase | 11.6 | 1.2 (±0.1) |
| Leucine aminopeptidase | 12 | 12 (±1) |
| Plasminogen activator (UCTA/mg) | 0.9 | 0.4 |

Intracellular level of several lysosomal and ekto-enzymes from elicited peritoneal macrophages obtained by in vivo injection of NSPD Specific activity is expressed as nanomoles of substrate hydrolyzed/min/mg of cellular protein; mean ±SD, except for plasminogen activator.

The potentialities of NSPD and others Nocardia fractions to detect tumors in vivo or ex vivo and some inflammatory states bring into play a population of mononucleated phagocyting cells among which activated macrophages.

These cells are able to fix those fractions in vitro as in

| | N. opaca fractions | | | | | |
|---|---|---|---|---|---|---|
| | Experiment 1 CW | | Experiment 2 NDCM | | Experiment 3 NSPD | |
| Treatment of mice | Mean tumor diameter | Mean weight of lungs | Mean tumor diameter | Mean weight of lungs | Mean tumor diameter | Mean weight of lungs |
| Oil-water emulsion | 19.2 ± 9 | 365 ± 10 | 22 ± 0.8 | 328 ± 38 | 18.7 ± 0.6 | 629 ± 90 |
| Culture medium | — | — | 21 ± 0.7 | 288 ± 26 | 18.5 ± 0.5 | 649 ± 66 |
| N. opaca fractions | 16.7 ± 0.7 | 315 ± 37 | 19.6 ± 0.53 | 262 ± 35 | 18.1 ± 0.3 | 502 ± 74 |
| Monokines | 17.5 ± 0.7 | 265 ± 40 | 18.9 ± 0.37 | 221 ± 21 | 18.1 ± 0.7 | 454 ± 83 |
| N. opaca fractions + monokines | 15.7 ± 0.8 | 229 ± 17 | 18.4 ± 37 | 211 ± 12 | 17.1 ± 0.5 | 353 ± 29 |

Effects of NCDM, NSPD, CW, monokines and the association of monokines and each N. opaca fraction, on the local tumor growth and lung metastatic spread of the 3LL tumor.

In case of rat metastatic rhabdomyosarcoma (9-4-(0)clone6), the tumor regression is practically total as result of a twice by week treatment during 2 months.

vivo then exhibit the characteristics of activated macrophages, i.e. a strong production of hydrogen peroxide ($H_2O_2$) and a glucose consumption increase.

| Treatment of rats | Number of rats with invasion of local lymph nodes | Individual count of lung tumoral nodules | Median |
|---|---|---|---|
| Oil-water emulsion | 7 | 7, 10, 19, 31, 36 45, 51, 66, 107, 155 | 40 |
| NSPD in oil- | 1 | 0, 0, 0, 0, 0 | 0 |

| Macrophages capacities | Control macrophages | NSPD stimulated Macrophages |
|---|---|---|
| $H_2O_2$ produced after 90 min of PMA triggering or zymosan triggering (nanomoles $H_2O_2$/100 μg | <1 | 30 (±5) |
| | <1 | 23 (±2) |

-continued

| Macrophages capacities | Control macrophages | NSPD stimulated Macrophages |
| --- | --- | --- |
| protein) | | |
| Glucose consumption (nanomoles/hours/100 μg protein) | 18 | 88 (±7) |

Reactive oxygen secretion and glucose consumption from elicited peritoneal macrophages obtained by in vivo injection of NSPD

We claim:

1. Aerosol composition for application to humans or animals comprising one or more soluble fragments of bacterial wall peptidoglycan or bacterial cell peptidoglycan, wherein the peptidoglycan includes NSPD, encapsulated in liposomes; and a carrier gas suitable for aerosol administration.

2. Aerosol composition according to claim 1, wherein, for in vivo imaging or ex vivo diagnosis of tumors, said one or more soluble fragments of bacterial wall peptidoglycan or bacterial cell peptidoglycan are labelled with a radioactive, paramagnetic, or fluorescent element.

3. Aerosol composition according to claim 1 for therapy wherein said soluble fragments of bacterial wall peptidoglycan or bacterial cell peptidoglycan are used for immunotherapy or as a targeted drug carrier, wherein a drug is bound to said soluble fragments.

4. Aerosol composition as claimed in claim 2, wherein the NSPD is labelled with $^{99m}$ technetium or with another emitter detectable by scintigraphy or counting.

5. Aerosol composition as claimed in claim 2, wherein the NSPD is labelled with a paramagnetic probe.

6. Aerosol composition as claimed in claim 2, wherein the NSPD is labelled with a fluorescent probe.

7. Aerosol composition as claimed in claim 1, wherein said liposome consists of at least one lipid having substantial surfactant properties with respect to cell tissue and is thus readily emulsifiable in cell tissue.

8. Aerosol composition as claimed in claim 7, wherein the liposome is a dipalmitoyl phosphatidylcholine/phosphatidylserine/cholesterol liposome.

9. Aerosol composition as claimed in claim 8, wherein the mole ratio of the components of the liposome is 4:1:5.

10. Aerosol composition as claimed in claim 1, wherein said NSPD is in combination with one or more products possessing substantial surfactant properties with respect to cell tissue.

* * * * *